(12) United States Patent
Adrian et al.

(10) Patent No.: US 7,844,473 B1
(45) Date of Patent: *Nov. 30, 2010

(54) SYSTEM FOR ALLOCATING HOME HEALTH SERVICES

(75) Inventors: Verne Adrian, St. Martinville, LA (US); Marie-Francoise Broussard, St. Martinville, LA (US); William Morris, New Iberia, LA (US); Keith G. Myers, Sunset, LA (US)

(73) Assignee: LHC Group, Inc., Lafayette, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/362,233

(22) Filed: Feb. 20, 2009

Related U.S. Application Data

(63) Continuation of application No. 10/261,701, filed on Sep. 30, 2002, now Pat. No. 7,505,916.

(60) Provisional application No. 60/326,416, filed on Oct. 1, 2001.

(51) Int. Cl.
*G06Q 50/00* (2006.01)

(52) U.S. Cl. .................... 705/2; 705/3; 705/4; 705/7; 705/10; 128/630; 128/920

(58) Field of Classification Search .................. 705/2, 705/3

See application file for complete search history.

(56) References Cited

U.S. PATENT DOCUMENTS

| | | | |
|---|---|---|---|
| 4,667,292 A | 5/1987 | Mohlenbrock et al. |
| 5,225,976 A | 7/1993 | Tawil |
| 5,301,105 A | 4/1994 | Cummings, Jr. |
| 5,307,262 A | 4/1994 | Ertel |
| 5,359,509 A | 10/1994 | Little et al. |
| 5,544,044 A | 8/1996 | Leatherman |
| 5,557,514 A | 9/1996 | Seare et al. |
| 5,794,220 A | 8/1998 | Hunt |
| 5,819,228 A | 10/1998 | Spiro |
| 5,915,241 A | 6/1999 | Giannini |
| 5,918,208 A | 6/1999 | Javitt |
| 6,012,035 A | 1/2000 | Freeman, Jr. et al. |
| 6,014,632 A | 1/2000 | Gamble et al. |
| 6,061,657 A | 5/2000 | Whiting-O'Keefe |
| 6,067,522 A | 5/2000 | Warady et al. |

(Continued)

OTHER PUBLICATIONS

Integrated Health Systems: Promise and Performance, Conrad, Douglas A.; Shortell, Stephen M.; Frontiers of Health Services Management; Fall 1996; 13, 1.

(Continued)

*Primary Examiner*—R. David Rines
(74) *Attorney, Agent, or Firm*—Jones, Walker, Waechter, Poitevent, Carrere & Denegre, L.L.P.

(57) ABSTRACT

A method in a computer system for optimizing allocation of a fixed medical payment to a variety of medical services. The method includes the steps of first selecting a standard rate representing an unadjusted amount of money to be received for the rendering of medical services. Next, the method generates an adjusted standard rate by adjusting the standard rate by at least one adjustment factor. The method then selects a base medical service rate from a plurality of medical service rates. Finally, the method divides the adjusted standard rate by the base medical service rate in order to generate a quantity of medical service points available.

15 Claims, 4 Drawing Sheets

U.S. PATENT DOCUMENTS

| | | |
|---|---|---|
| 6,266,645 B1 | 7/2001 | Simpson |
| 6,594,668 B1 | 7/2003 | Hudy |
| 2002/0077854 A1 | 6/2002 | Porterfield |
| 2002/0120466 A1 | 8/2002 | Finn |

OTHER PUBLICATIONS

Statement of Commercial Use on or about Oct. 1, 2000 submitted by Lance A. Foster.

SYSTEM FOR ALLOCATING HOME HEALTH SERVICES

This application is a continuation of pending U.S. application Ser. No. 10/261,701, filed on Sep. 30, 2002, which claims priority to U.S. Provisional Application Ser. No. 60/326,416, filed on Oct. 1, 2001; each are incorporated by reference in their entirety.

I. FIELD OF INVENTION

The present invention relates to healthcare management in the Medicare Home Health Industry. In particular, the present invention provides a method of allocating medical services based upon an anticipated reimbursement for Medicare Home Health beneficiaries under a Perspective Pay System.

II. BACKGROUND OF THE INVENTION

On Oct. 1, 2000 the U.S. Healthcare Financing Administration (referred to generally herein as simply "Medicare") changed the reimbursement terms for services provided to Medicare beneficiaries (also referred to as patients herein) who receive services provided by Medicare licensed Home Health Agencies (HHAs). Details of the change from the previous system which was called the Interim Payment System (IPS) to this latest system, referred to as the Prospective Pay System (PPS), are described in the Final Rule published in the Federal Register in June 2000. The methods previously employed under IPS by Home Health Agencies for projecting costs and reimbursements are rendered obsolete by the change to PPS.

Under PPS, the HHA is responsible for nearly all post acute patient care, including outpatient therapy and some supplies, that the patient receives in 60-day increments. These 60-day increments are called "episodes." There are some exceptions which are not important to understanding the present invention, but nevertheless may be found in the appropriate Federal Register entries. Under PPS, the typical HHA must consider a multitude of conditions to determine the expected payment for each 60 day episode of care. Accordingly, the reimbursement is based on a number of factors. The first of these factors, the Home Health Related Group (HHRG), is the general category that determines a patient's need for services. The HHRG is assigned to a patient based on the result of an Outcome and Assessment Information Set (OASIS) Certification Assessment. This OASIS Assessment is performed in the patient's home at the initial Start of Care (SOC) or upon Recertification, i.e. the beginning of subsequent and contiguous 60-day episodes. These assessment types are termed as Reason For Assessment 1 (RFA 1) and RFA 4, respectively. To determine the expected reimbursement for each episode, the HHA must take results of the RFA 1 or RFA 4 assessments. The result of these assessments determine to which HHRG the patient is assigned.

At present, the Healthcare Administration has defined 80 HERGs. Each 60-day assessment assigns a specific HHRG to a patient. The HHRG has three major components, each correlating to patient needs. These components are Clinical, Functional, and Service. The Clinical and Service components are assigned values from 1 to 3. The Functional component is assigned values from 1 to 4. The value assigned to each component is an indication of patient need relative to that component. For example, a HHRG of C3F1S0 would indicate higher anticipated need for the Clinical component and a lower need for the Service component. Each HHRG is assigned a factor called the "Case Mix Weight." This Case Mix Weight is multiplied by a standard rate which is the amount Medicare uses as a starting point for calculating the reimbursement to HHA's for any 60 day episode. Prior to Apr. 1, 2001 all HHAs had the same single standard rate of $2,115.30. As of Apr. 1, 2001 there are two standard rates: MSA standard rate and a non-MSA (i.e. Rural) standard rate. At that time, the non-MSA standard rate was $2,378.02 and the MSA standard rate was set at $2161.84. However, this has increased over time and as of Oct. 1, 2002 the non-MSA standard rate will be $2,375.33 and the MSA standard rate will be $2,159.39. As an example, for a patient who had his last billable visit on Dec. 1, 2000, the standard The Case Mix Weight for HHRG C3F1S0 was 1.2922. Thus, the unadjusted expected reimbursement for this patient is $2115.30*1.2922=$2733.39.

This unadjusted reimbursement rate is then further adjusted by additional factors. One such factor is the "wage index." Medicare recognizes that different geographical regions have different market wages customarily paid to the nurses, therapists, medical social workers and home health aides to provide direct, hands-on skilled clinical and unskilled personal care services. Medicare has determined that for FY 2001 the portion of the standard PPS rate that may be adjusted by geographical region is 77.668%. The standard PPS rate may be considered as consisting of the two components. First, there is the "labor portion" which consists of agency expenses attributed to direct patient care (e.g. the direct cost of placing a caregiver in the home to provide hands-on care). Using a patient's residence, Medicare determines a multiplication factor using a table referred to as the Metropolitan Statistical Areas (MSAs). The values in this table are issued by the Office of Management and Budget (OMB). Second, there is the non-labor portion (e.g. an amount not adjusted and considered as the reimbursement for the non-labor related costs).

Thus the PPS reimbursement rate is generally determined by multiplying a standard rate by the case mix weight and then further adjusting this value by two additional adjustment factors, namely the labor/non-labor portion and the wage index. As an illustrative example, the formula for a wage adjusted PPS may be represented as follows:

$$(CaseMixWeight*PPSRate*LaborPortion*WageIndex)+ CaseMixWeight*PPSRate*NonLaborPortion).$$

A numerical example based on a 60-day episode governed by the PPS and adjustment factors in effect as of Dec. 29, 2000 for a patient residing in Lafayette, La. would be as follows:

1.2922=Case Mix Weight (assuming the applicable HHRG is C3F1S0)
$2115.30=Standard National PPS Rate
0.77668=Labor Portion
0.22332=Non labor portion
0.8340=MSA adjustment factor for the patient's location (i.e. wage index)

The expected reimbursement for the 60-day episode would be:

$$(1.2922*2115.30*0.77668*0.8340)+(1.2922*2115.30*0.22332)= \$2380.98$$

There may be numerous prior art strategies to generate reports based on the anticipated reimbursement and the anticipated costs to provide clinical services. One method would be to divide the total anticipated reimbursement by the average cost of all of the visits. However, this approach does not take into account the differences in the costs for providing different types of care. For example a Medical Social Worker is often five times more expensive than sending a home health aide. An additional weakness of this strategy is the HHA employee who is scheduling visits for the 60-day episode uses reimbursement dollars as the budgeting tool. This is an inherent weakness in that it may lead the employee to believe that patient care is being rationed strictly according to reimbursement and that patient health care needs are less important than the reimbursement. Of course, this is an undesirable result since rationing care is completely contrary to clinical training. Additionally, PPS was constructed with the goal that within a HHA, patients who require more intensive care are "subsidized" by patients who require less intensive care. Nor do prior art methods readily take into account that reimbursement amounts must not only cover the direct cost of the care giver's salary and expenses, but must also cover the indirect costs of the HHA. Moreover, patients with high therapy needs will require more costly treatment which should be taken into account when allocating services. What is needed in the art is a method which aides HHA personnel in best allocating the number and type of care provider visits (e.g. nurse, therapist, etc.) a patient should receive while taking into account the budgetary constraints of the reimbursement system.

III. SUMMARY OF THE INVENTION

The present invention provides a method in a computer system for optimizing allocation of a fixed medical payment to a variety of medical services. The method includes the steps of first selecting a standard rate representing an unadjusted amount of money to be received for the rendering of medical services. Next, the method generates an adjusted standard rate by adjusting the standard rate by at least one adjustment factor. The method then selects a base medical service rate from a plurality of medical service rates. Finally, the method divides the adjusted standard rate by the base medical service rate in order to generate a quantity of medical service points available.

IV. BRIEF DESCRIPTION OF THE DRAWINGS

FIG. 4 is an illustrative example of a data entry screen a user of the present invention might utilize.

FIG. 5 is a further illustrative example of a data entry screen a user of the present invention might utilize.

V. DETAILED DESCRIPTION OF THE INVENTION

Figure 1:
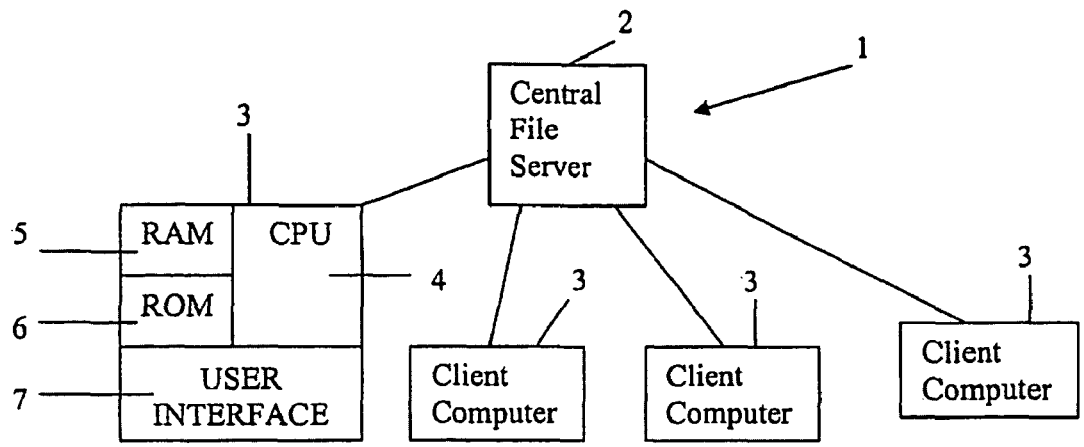
FIG. 1 is a block diagram of a LAN which could employ the present invention.

The present invention provides a method of converting the expected PPS reimbursement dollars into alternative units which allows HHA personnel to better allocate health care services to the patient. Typically, the method will be realized through software operating on a general purpose computer or a network of general purpose computers. Thus, in a simplified illustration, FIG. 1 shows a local area network (LAN) 1 which could comprise a file server 2 and a plurality of client computers 3. Each client computer 3 could be a conventional desktop computer having a CPU 4, RAM 5, ROM 6, and a User Interface 7 such as a keyboard, monitor, and mouse. While the present invention could be utilized on a single computer, the large number of anticipated medical records makes it desirable to use a central file server with hard drives or other high capacity storage mediums.

To practice the method of the present invention, it is first necessary to calculate the anticipated adjusted standard rate of reimbursement as described above. To carry out this computation, the method will require values for the case mix weight, the PPS standard rate, the labor and non-labor portion, and the wage index associated with a patient's location. Additionally, patient identification information and medical assessment information will be required. In one embodiment of the invention, this information may be manually entered into the computer as part of the program of the present invention. However, in a preferred embodiment, at least some of this information will already have been entered in connection with the running of another program such as the HAVEN software provided by Medicare. The HAVEN software was developed to provide HHA's with software for data entry, editing, and validation of OASIS data. It includes information on setting up the software, defining agency and employee information, entering patient and assessment data, and data management functions.

While the present invention may import patient identification information from the HAVEN software, HAVEN provides little information related to the required adjustment factors beyond the HHRG. The labor/non-labor portions currently in effect will be stored in memory and will only be altered when Medicare adjusts this ratio. In one embodiment, the invention will provide computer readable look-up tables such as seen in Table 1 below.

TABLE 1

| Eff. Date | HHRG | Case Mix Weight | Ther. Portion | Non Ther. Portion |
|---|---|---|---|---|
| Jan 1, 1996 | C0F0S0 | 0.5285 | 0.00% | 30.00% |
| Jan 1, 1996 | C0F0S1 | 0.6074 | 0.00% | 30.00% |
| Jan 1, 1996 | C0F0S2 | 1.4847 | 25.00% | 20.00% |
| Jan 1, 1996 | C0F0S3 | 1.7384 | 25.00% | 20.00% |
| Jan 1, 1996 | C0F1S0 | 0.8213 | 0.00% | 30.00% |
| Jan 1, 1996 | C0F1S1 | 0.7022 | 0.00% | 30.00% |
| Jan 1, 1996 | C0F1S2 | 1.5798 | 25.00% | 20.00% |
| Jan 1, 1996 | C0F1S3 | 1.8313 | 25.00% | 20.00% |
| Jan 1, 1996 | C0F2S0 | 0.7249 | 0.00% | 30.00% |

Table 1 will specify the appropriate case mix weight for each HHRG and the effective date of that case mix weight. While Medicare specifies 80 HHRGs, the few shown in table 1 are sufficient for illustrative purposes. The remaining HHRGs and their case mix weight are readily available from the Federal Register Vol. 65, No. 128, Monday Jul. 3, 2002. The columns labeled "Ther." and "Non Ther." portion are explained below. The wage index will be obtained in a similar manner with a computer readable look-up table having information such as seen in Table 2.

TABLE 2

| Zip Code | State | City | Parish/Count | MSA # | Wage Index |
|---|---|---|---|---|---|
| 70006 | LA | Metairie | Jefferson | 5580 | 0.9295 |
| 70009 | LA | Metairie | Jefferson | 5580 | 0.9295 |
| 70010 | LA | Metairie | Jefferson | 5580 | 0.9295 |
| 70011 | LA | Metairie | Jefferson | 5580 | 0.9295 |
| 70030 | LA | Des Allemands | Saint Charles | 5580 | 0.9295 |
| 70032 | LA | Ama | Saint Charles | 5580 | 0.9295 |
| 70032 | LA | Arabi | Saint Bernard | 5580 | 0.9295 |
| 70033 | LA | Metairie | Jefferson | 5580 | 0.9295 |

Medicare provides information concerning the wage index corresponding to particular MSAs. However, Medicare's wage indices is generally referenced by a county (or parish in Louisiana) designation. In a preferred embodiment of the present invention, the county designation is cross referenced with the zip codes following within the appropriate county. Therefore, entering a patient's zip code will allow the invention to select the proper wage index for the patient's location. As with Table 1, Table 2 represents only a few of the many MSAs and wage indices established by Medicare and published in the Federal Register. Once the factors needed to determine the adjusted standard rate are supplied, the expected reimbursement amount may be calculated as described above.

In fully understanding the PPS, it is important to recognize that the total health care costs incurred by HHA's may be divided up into direct and indirect costs. Direct costs include the actual costs of placing a clinician in the home to provide hands-on care. Examples of these costs can include salary and benefits, mileage, professional liability and workman's compensation insurance. Examples of clinicians typically employed by HAA's are registered nurses (RN's), licensed practical nurses (LPN's), physical therapists (PT's), physical therapy assistants (PTA's), occupational therapists (OT's), occupational therapy assistants (OTA's), speech therapists/speech pathologists (ST's), medical social services (MSW's), and home health aides (HA's). As an example, the total direct costs (in dollars) to the HHA of a clinician visit to a home health patient could be as follows for each of the various clinicians:

TABLE 3

|  | RN | LPN | HA | PT | PTA | OT | OTA | ST | MSW |
| --- | --- | --- | --- | --- | --- | --- | --- | --- | --- |
| Direct Cost | 60.00 | 32.00 | 18.00 | 68.00 | 65.00 | 70.00 | 67.00 | 70.00 | 82.00 |

The total direct costs for a home visit by each of the clinicians listed above may be referred to as a medical service rate. On the other hand, non-direct costs would include costs such as clinical managerial costs, non-clinician personnel costs, office rent, utilities, telephones, salaries to non-clinician office staff and others not directly involved in patient care. The allocation of indirect costs by the present invention is discussed in greater detail below.

One aspect of the present invention is the allocation of direct costs by the selection of a base medical service rate and the normalization of the other medical service rates relative to the base medical service rate (also referred to herein as the "base rate"). Moreover, the utility of the present invention is enhanced if the lowest of the medical service rates is chosen as the base rate. The division of each of the medical service rates by the base rate will provide a number representing the unit cost (relative to the base rate) of a clinician visit to a home health patient. This unit cost number may be referred to in terms of "medical service points" (MSPs). Table 4 shown below illustrates how the medical service rates from Table 3 will be divided by the lowest medical service rate (the HA rate of $18 in this example) to achieve a quantity of MSP related to each type of clinician.

TABLE 4

|  | RN | LPN | HA | PT | PTA | OT | OTA | ST | MSW |
| --- | --- | --- | --- | --- | --- | --- | --- | --- | --- |
| Direct Cost | 60.00 | 32.00 | 18.00 | 68.00 | 65.00 | 70.00 | 67.00 | 70.00 | 82.00 |
| MSP | 2.33 | 1.78 | 1 | 3.78 | 3.61 | 3.89 | 3.72 | 3.89 | 4.56 |

By converting the costs associated with each clinician visit into MSPs, the financial managers of HHAs and the clinicians have a consistent method of determining the resources necessary to provide appropriate care as well as the number of MSPs expected to be expended. This desired effect is realized without assigning dollar values. Additionally, this allows the scheduling HHA to best serve the patient's needs by seeking physician orders that allow flexibility in the types of services ordered to meet the individual patient's need and still maintain close financial oversight on the costs of providing appropriate services.

A further aspect of the present invention is converting the PPS adjusted standard rate dollar amount to a total number of MSPs available. This may be done by dividing the adjusted standard rate by the base rate. Thus, in the above example wherein the adjusted standard rate was $2380.98, the total number of MSPs represented by this projected reimbursement would be $2380.98 divided by the base rate of $18 or 132.2 MSPs. In effect, by dividing a patient's adjusted standard rate dollar amount by the base rate, the standard rate is converted to a number of MSPs that reflects a dollar break-even value.

Of course, as suggested above, the entire number of MSPs represented in an adjusted standard rate cannot be entirely expended on direct costs. The direct costs only account for a portion of the cost of providing care and indirect costs must also be accounted for when providing home health medical care. However, the present invention again greatly assists HHAs in determining what portion of the adjusted standard rate reimbursement will be allocated to indirect costs. Thus by multiplying the total number of MSPs available to a patient by the percentage which direct costs are expect to be of total costs, the HHA is provided with an expected number of MSPs available for clinician visits as a guide for use in scheduling these visits.

However, in a preferred embodiment of the present invention, the division of direct and indirect costs are subsumed in the allocation of therapy versus non-therapy clinician services. The method also has the benefit of assisting HHAs in allocating health care resources to patients with high therapy needs, such therapy needs being provided by clinicians such as physical therapists & assistants, occupational therapists & assistants, and speech pathologists. Certain HHRGs are assigned significantly higher reimbursement based on a high therapy need. These HHRGs are identified by the last digit (following the "S") in the HHRG classification number. Thus, a HHRG classification number with a S2 or S3 would be considered a high therapy case mix (e.g. C0F2S3). Therefore, the number of MSPs allocated for direct costs (i.e. clinician visits) may be further broken down into MSPs allocated for therapy and non-therapy visits, thus allowing the HHA to fine tune the scheduling for the therapy and the non-therapy components. As another illustrative example, let it be assumed that 132 total MSPs are available for a patient classified in a high therapy HHRG such as C2F2S3. If it is determined that 45% of the MSPs should be devoted to direct costs with 20% of the direct costs devoted to non-therapy services and 25% devoted to therapy services, the HHA can readily determine that 26.4 MSPs may be devoted to non-therapy clinician visits and 33 MSPs devoted to therapy clinician visits. Table 1 illustrates one example of how therapy and non-therapy portions could be allocated based upon a given HHRG. In Table 1, HHRGs with S2 and S3 values indicate that the therapy portion should be 25% and the non-therapy portion 20%. Likewise, HHRG's having S0 and S1 values not indicating a need for therapy visits might have 30% budgeted to non-therapy clinicians. It can also be seen how the sum of the therapy and non-therapy portions can constitute the percentage of direct costs. As will be seen below, this allows the total MSPs available to be multiplied by the therapy and non-therapy portions and result in a some resources still being allocated to indirect costs.

A still further advantage gained from converting dollar amounts in MSPs arises when the HHA wishes to provide other services to a home health patient which are not necessarily base upon clinician visits. For example, one such "non-clinical" service the HHA may wish to provide patients is an emergency notification service. This service could be of the type known in the art whereby the patient wears a transmitter which can be activated to call for help when the patient is in an emergency situation. Alternatively, there are systems which remind patients (typically elderly patients) when to take prescribed medications. The present invention's use of MSPs allows the cost of such non-clinical services to easily be allocated as part of the costs for which the HHA must account. For purposes of the present description, the cost of these nonclinical services will be allocated using what will be termed an optional across-the-board adjustment factor (OABAF). The number of MSPs represented by the OABAF is most preferably factored out of both the therapy and the non-therapy portions of the direct costs. To accomplish this, two further terms will be defined, the "therapy deduction" and the "non-therapy deduction." The therapy deduction will equal the therapy portion divided by the sum of the therapy and non-therapy portions. Likewise, the non-therapy deduction will equal the non-therapy portion divided by the sum of the therapy and non-therapy portions. As an example, if the therapy portion were equal to 0.20 and the non-therapy portion equal to 0.25, the therapy deduction will equal 0.20/(0.20+0.25) while the non-therapy deduction equals 0.25/(0.20+0.25). After the calculation of these numbers, adjusted available therapy MSP's and non-therapy MSP's may be calculated by subtracting from the initial MSP's the product of the deductions and an "option rate". Thus, the number of adjusted available therapy MSP's is equal to the initial therapy MSP's minus the therapy deduction times the option rate. Likewise, the number of adjusted available non-therapy MSP's is equal to the initial non-therapy MSP's minus the non-therapy deduction times the option rate. In a preferred embodiment, the option rate will be set equal to ten (10), but could vary based on the value of the non-clinical services provided.

Figure 2:
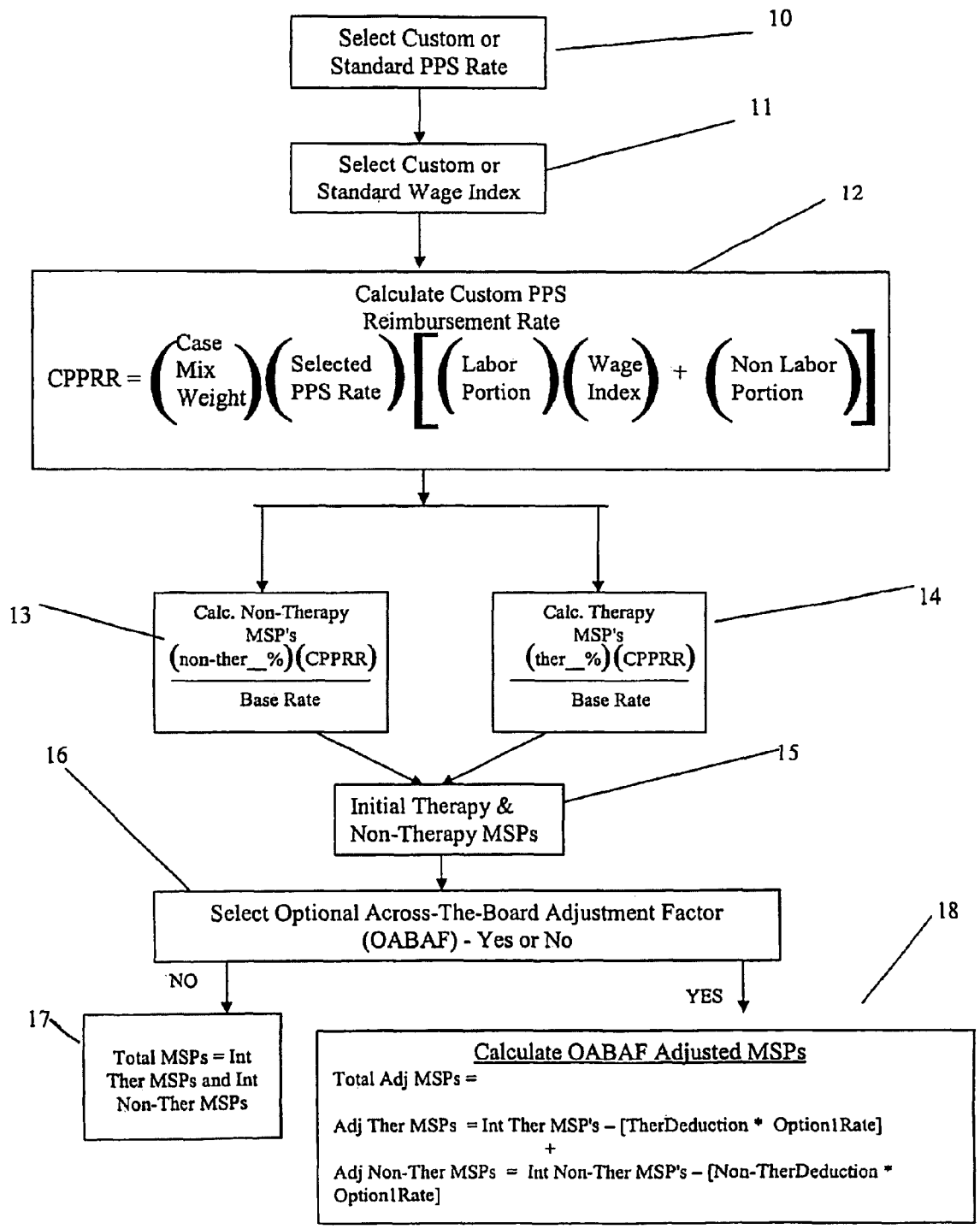
FIG. 2 is a flow chart illustrating the calculation of MSPs according to the present invention.

FIG. 2 is a flow chart which illustrates the above describes steps carried out in the method of the present invention. In step 10, the HHA employee or computer user will select whether calculations will be made with the standard PPS reimbursement rate or a custom reimbursement rate. There may be instances when, although very closely geographically situated (e.g. different streets in the same locality), one patient will be considered by Medicare regulations to be residing in a rural area (having one standard PPS rate) while another is considered to be residing in an urban area (having a second standard PPS rate). To provide equal care to persons living in the same geographical area, the HHA may wish to treat these patients as having the same PPS reimbursement rate. Step 11 will be a similar procedure wherein the user selects the standard wage index or can select a custom wage index which the HHA believes more realistically reflects the local wage conditions. Next, step 12 illustrates how the Custom PPS Reimbursement Rate (CPPRR) will be calculated. The labor portion multiplied by the wage index is added to the non-labor portion. This number is then multiplied by the PPS rate selected in step 10 and the case mix weight incorporated from the patient's HHRG. In steps 13 and 14, the respective non-therapy and therapy MSPs are calculated. This calculation consists of multiplying the non-therapy percentage (or therapy percentage) by the CPPRR and then dividing this product by the medical services base rate. The addition of these numbers will reflect the initial MSPs available as suggested in step 15. Step 16 will inquire as to whether an OABAF will be applied in this patient's case. If no, step 17 indicates that the total MSPs available will equal the initial MSPs found in step 15. If step 16 prompts a yes response, the total MSPs will be equal to the sum of the adjusted therapy MSP's and adjusted non-therapy MSP's.

As an example of the calculation of adjusted therapy and non-therapy MSP's, let it be presumed that the CPPRR was calculated in accordance to step 12 to be equal to $4,000.00. Further allow the therapy portion to be 0.20, the nontherapy portion to be 0.15, the base rate equal to 18 and the option rate equal to 10. The adjusted therapy MSPs will be calculated as follows:

$$\frac{(CPPRR * \text{Ther\_Portion})}{\text{BasePoints}} - (\text{TherDeduction} * \text{Option1Rate}) \frac{(4,000.00 * .20)}{18} - \left(\frac{.20}{.35} * 10\right) = 38.73$$

The NonTherapy MSPs will be calculated as follows:

$$\frac{(PPS * \text{NonTher\_Portion})}{\text{BasePoints}} - (\text{NonTherDeduction} * \text{Option1Rate}) \frac{(4,000.00 * .15)}{18} - \left(\frac{.15}{.35} * 10\right) = 29.05$$

Another function of the present invention will be a method for prompting HHA personnel inputting data to ensure the proper number and type of clinician visits are scheduled for a particular patient. As previously mentioned, the HHRG is made up of three components for the purpose of determining reimbursement: C=Clinical, F=Functional, and S=Service. Depending on how BHA personnel respond to queries in the OASIS assessment, the clinical, functional, and service components will receive different values. As an example, the OASIS question M0825 is: "Does the care plan of the Medicare payment period for which this assessment will define a case mix group indicate a need for therapy (physical, occupational, or speech therapy) that meets the threshold for a Medicare high-therapy case mix group?" If this question is answered in the affirmative, then the patient receives an assessment score of S2 or S3 in the HHRG which signifies a higher need for therapy. However, the HHA will receive a higher reimbursement if and only if HHA provides the number of therapy visits in any combination that meets a threshold number of visits set by Medicare. Presently, the threshold is 10 visits or more (although this threshold may of course change in the future). If the HHA employee scheduling the number and type of clinician visits to the patient does not schedule at least 10 therapy visits, the program will prompt the employee with a message such as "Caution, You must schedule at least 10 therapy visits!". Naturally, this therapy threshold will be readily adjustable in the present invention since it is likely that governmental regulations governing the therapy thresholds will be likely changed in the future.

Figure 3:
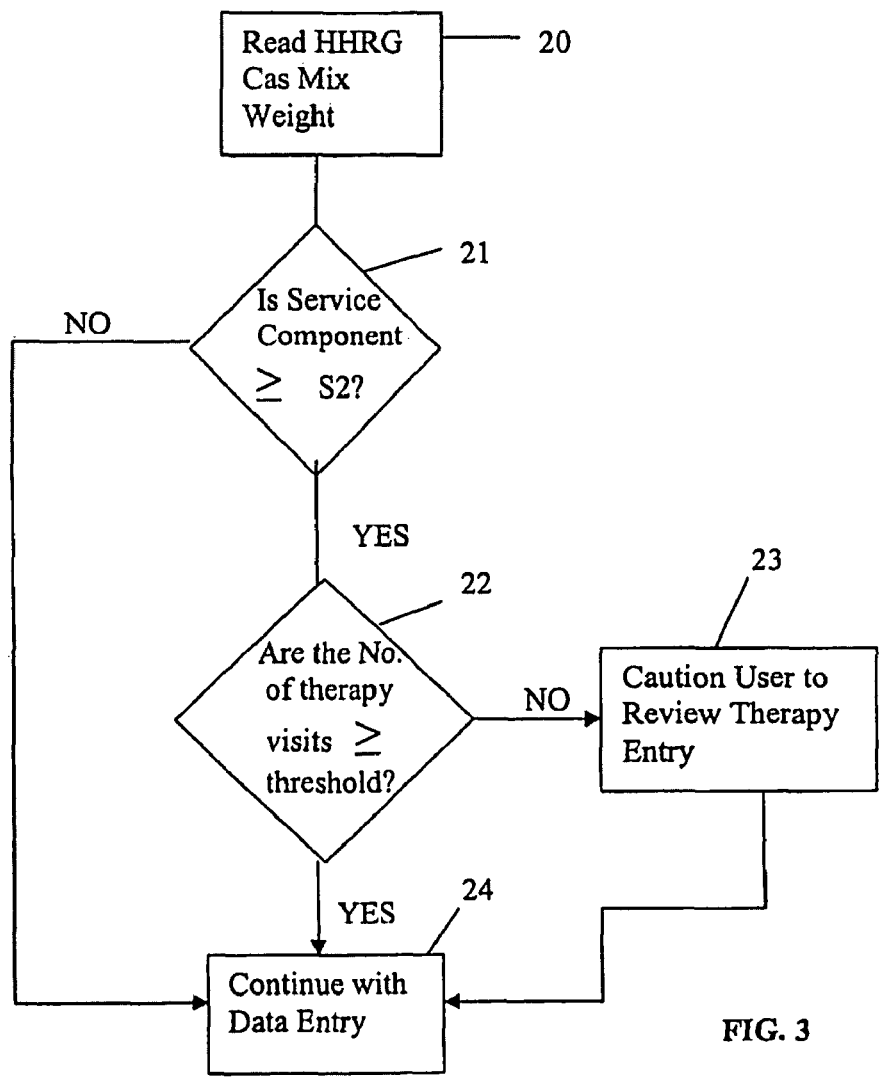
FIG. 3 is a flow chart illustrating a method of reminding the user to input certain data.

FIG. 3 illustrates the sequence of steps associated with this aspect of the present invention. In step 20, the case mix weight of the selected HHRG will be read. If the service component of the case mix weight is not classified S2 or higher in step 21, then the method will continue with data entry in step 24. If the service component is S2 or higher, step 22 will determine whether the number of therapy visits selected equals or exceeds the predetermined threshold. If this determination is "yes", data entry is continued in step 24. If this determination is "no", step 23 prompts the user to review the number of therapy visits selected and thereafter data entry is continued.

Figure 4:
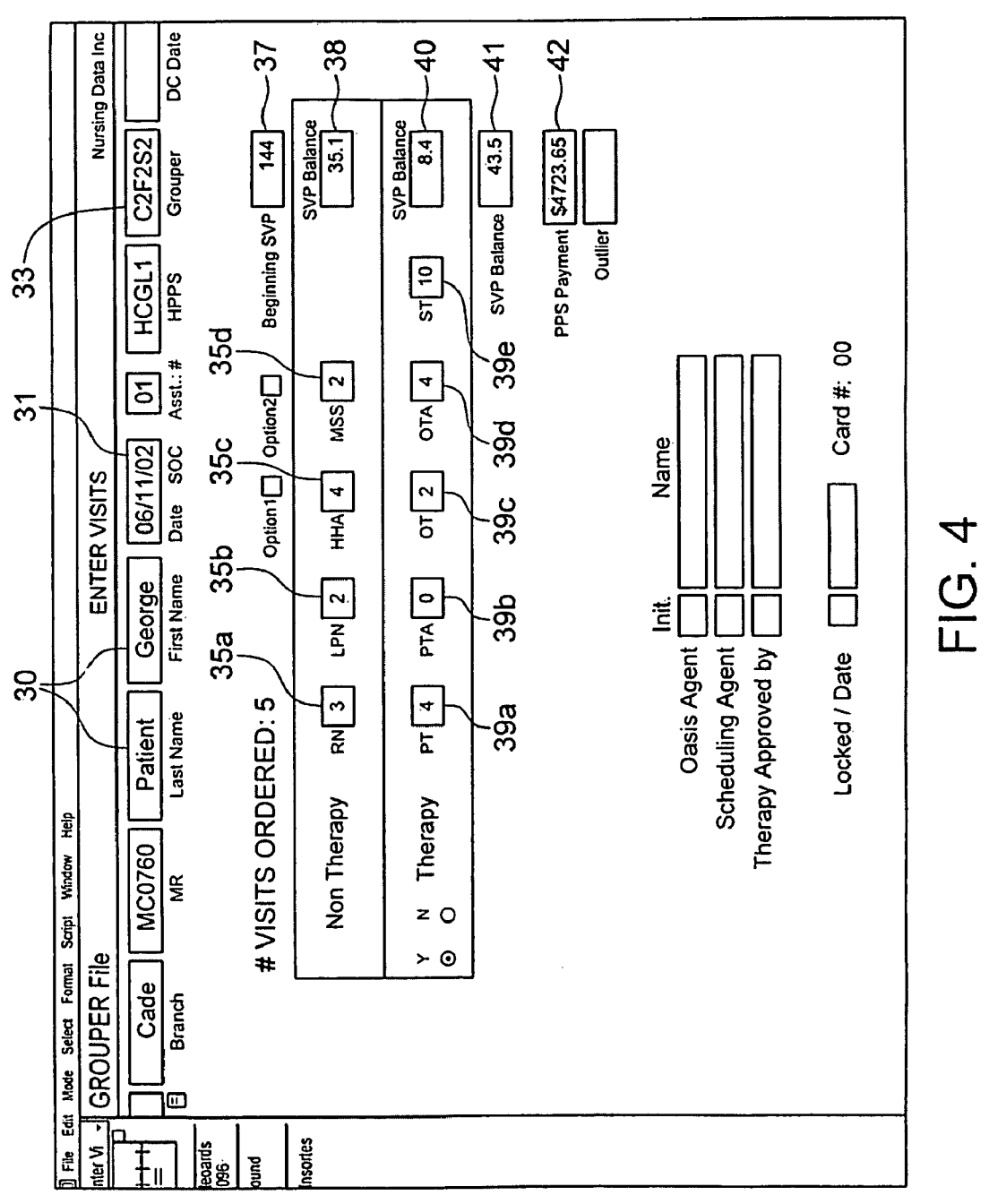

FIG. 4 is a representation of the typical data entry screen a user would see in one computer implemented embodiment of the present invention. There would be several fields identifying patient data such as name (fields 30), start of care date 31, and the HHRG 33. A field 37 will indicate the total MSPs (shown as "SVPs" in FIG. 4) available for use. Another set of fields will relate the number of non-therapy clinician visits being scheduled for the patient. Field 35a reflects the number of RN visits, field 35b LPN visits, field 35c HHA visits, and field 35d MSS visits. Field 38 will indicate the number of non-therapy MSPs available after subtracting out the MSPs associated with the visits reflected in fields 35a-35d. In a similar manner, a set of fields will relate the number of therapy clinician visits being scheduled for the patient. Field 39a reflects the number of PT visits, field 39b PTA visits, field 39c OT visits, field 39d OTA visits, and field 39e ST visits. Field 40 will indicate the number of therapy MSPs available after subtracting out the MSPs associated with the visits reflected in fields 39a-39e. The sum of fields 38 and 40 will appear in field 41. The number appearing in Field 41, the MSP (or SVP) Balance, could be negative indicating that the types and numbers of visits predicted exceeds the number of MSPs and therefore the dollar amount allocated for direct costs for this HHRG. Field 42 will reflect the total PPS payment calculated for this patient during the present episode. Fields 38, 40, and 41 will preferably be updated as the numbers in fields 35 and 39 are altered. It can be seen how this allows the HHA to enter different combinations of clinician visits and immediately determine what effect this will have for budgetary purposes by observing how the sum of MSP's is altered.

Figure 5:
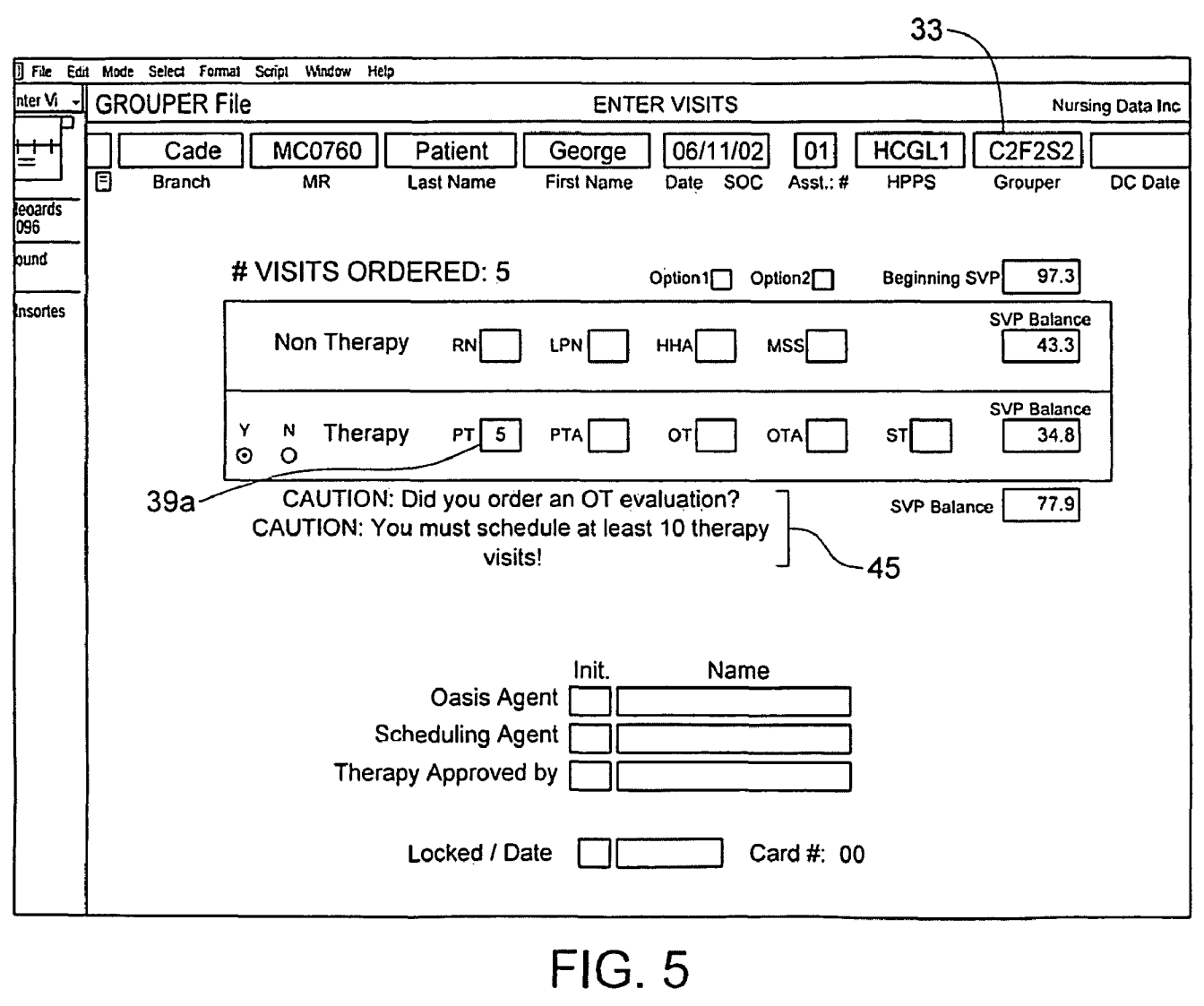

FIG. 5 is another typical data entry screen associated with the routine described in reference to FIG. 3 for preventing the inadvertent entry of too few therapy visits. It can be seen that the HHRG in field 33 is C2F2S2, thus indicating a patient classified as having a higher therapy need. However, the only therapy visits entered are 5 physical therapy visits in field 39a. In this situation, the program will display a notice in field 45 to the effect that less than 10 therapy visits have been scheduled. Thus, the HHA employee scheduling clinician visits is immediately aware that a sub-optimal number of therapy type visits is being scheduled.

While the present invention has been described with examples of specific embodiments, the invention is not limited to these particular configurations. Those skilled in the art will recognize many variation of the described embodiment which could come within the scope of the claimed invention. For example the experienced home health clinician usually can more often than not reasonably predict the number and types of services a patient will require over the 60 day episode assuming no intervening, unexpected events transpire. If when entering the predicted number of visits the MSP Balance is abnormally high or low, this will prompt the aware clinician to reevaluate the OASIS data. An error in entering a single data field in the OASIS assessment may result in an unusually large balance—either negative or the positive. This large balance prompts the clinician to verify the accuracy of the OASIS data set or the correct entry of the data into the OASIS software. Very rarely is the large balance justified but rather there was usually either a data collection or data entry error. Another tool the MSP invention makes possible is the ability to generate reports on the average case mix per OASIS collection agent over a period of time. If an agency randomly selects patients for the OASIS collection agents, the HHA sees patients in the same general geographical area for generally the same physicians one would expect about the same average MSP numbers for the OASIS collection agents (assuming a large enough sample). If the MSP numbers developed by a particular collection agent are significantly different from other collection agents, then a review of the quality and accuracy of the agent's data gathering skills may be warranted. Another benefit this tool makes possible is creating MVP balances in the aggregate that may assist the creation of budgets, predict the need for staffing, and justify expenses based on actual patient needs. The significance of this last advantage can not be overstated. To that end, the invention provides the missing link between the clinical, quality assurance, and financial departments in a HHA. Heretofore, this link has been missing and the use of this tool in this manner greatly assists the HHA in creating and maintaining clinical, ethical, and fiscal accountability. All such alternatives and modifications to the described embodiments and the advantages flowing therefrom are intended to come within the scope of the following claims.

We claim:

1. A computer system for optimizing allocation of a fixed medical payment to a variety of medical services, said system comprising:
   a. a means for processing data;
   b. a means for storing data on a storage medium;
   c. a means for providing a standard rate representing an amount of money to be received for the rendering of medical services;
   d. a means for providing a base medical service rate;
   e. a means for dividing said standard rate by said base medical service rate to generate a quantity of medical service points;
   f. a means for allocating at least a portion of said medical service points for visits by a clinician to a patient;
   g. a means for assigning a number of clinician visits to a patient and a number of medical service points from said portion which are associated with said clinician visits;
   h. a means for generating a schedule according to said assignment of clinician visits and associated medical service points; and
   i. a means for displaying to a user data related to said schedule.

2. The computer system of claim 1, further including a means for allocating a given number of said medical service points for each visit by a home health clinician to a home health patient.

3. The computer system of claim 1, wherein said base medical service rate is the lowest of a plurality of medical service rates from which said base medical service rate is selected.

4. The computer system of claim 3, further including a means for dividing each of said medical service rates by said base medical service rate so as to represent all of said medical service rates in medical service points.

5. The computer system of claim 1, further including a means for adjusting said standard rate by a wage index.

6. The computer system of claim 1, wherein said standard rate is a 60 day episode.

7. The computer system of claim 1, wherein said clinician visits include at least two from the group consisting of registered nurses, licensed practical nurses, physical therapists, physical therapy assistants, occupational therapists, occupational therapy assistants, speech therapists, medical social workers, and home health aides.

8. The computer system of claim 1, wherein a user interface allows a user to enter a number of clinician visits and displays a number of medical service points associated with said number of clinician visits and a total number of medical service points utilized and remaining to be utilized.

9. A computer system for optimizing allocation of a fixed medical payment to a variety of medical services, said system comprising:
   a. a database of patient records;
   b. a processor running software capable of performing at least the steps of:
      i. providing a standard rate representing an amount of money to be received for the rendering of medical services based upon data from a patient record;
      ii. dividing said standard rate by a base medical service rate to generate a quantity of medical service points;
      iii. allocating at least a portion of said medical service points for visits by a clinician to a patient;
      iv. calculating, based upon a number of clinician visits assigned to a patient, a number of medical service points associated with said clinician visits;
      v. generating a schedule according to said assignment of clinician visits and associated medical service points; and
   c. a user interface allowing a user to interact with said schedule, including entering a number of clinician visits and said interface displaying a number of medical service points associated with said number of clinician visits.

10. The computer system according to claim 9, wherein said schedule includes a total number of medical service points utilized and remaining to be utilized.

11. The computer system according to claim 9, wherein said database, processor, and user input are an integrated system at one location.

12. The computer system according to claim 9, wherein said user interface is located remotely from said database.

13. The computer system according to claim 12, wherein said database and processor are at one location.

14. A computer system for optimizing allocation of a fixed medical payment to a variety of medical services, said system comprising:
   a. at least one client computer comprising a user interface allowing a user to enter a number of clinician visits and displaying a number of medical service points associated with said number of clinician visits and a total number of medical service points utilized;
   b. a server computer communicating with said at least one client computer such that the system performs at least the steps of:
      i. providing a standard rate representing an amount of money to be received for the rendering of medical services based upon data from a patient record;
      ii. dividing said standard rate by a base medical service rate to generate a quantity of medical service points;
      iii. allocating at least a portion of said medical service points for visits by a clinician to a patient;
      iv. calculating, based upon a number of clinician visits assigned to a patient, a number of medical service points associated with said clinician visits; and
      v. generating a schedule according to said assignment of clinician visits and associated medical service points.

15. A computer system for the allocation of a fixed medical payment to a variety of medical services, said system comprising
   (a) a database comprising a plurality of patient records;
   (b) a server computer comprising a processor and associated software performing at least the steps of:
      i. providing a standard rate representing an amount of money to be received for the rendering of medical services based upon data from a patient record;
      ii. dividing said standard rate by a base medical service rate to generate a quantity of medical service points;
      iii. allocating at least a portion of said medical service points for visits by a clinician to a patient;
      iv. calculating, based upon a number of clinician visits assigned to a patient, a number of medical service points associated with said clinician visits;
      v. generating a schedule according to said assignment of clinician visits and associated medical service points; and
      vi. transmitting said schedule to a remote client computer.

* * * * *